United States Patent
Suzuki et al.

(10) Patent No.: US 7,915,389 B2
(45) Date of Patent: Mar. 29, 2011

(54) ANTI-ACHARAN SULFATE ANTIBODY AND ITS APPLICATION

(75) Inventors: Kiyoshi Suzuki, Higashiyamato (JP); Takeshi Ishimaru, Higashiyamato (JP); Koji Yamamoto, Higashiyamato (JP); Yeong Shik Kim, Seoul (KR)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 121 days.

(21) Appl. No.: 12/297,048

(22) PCT Filed: Apr. 27, 2007

(86) PCT No.: PCT/JP2007/059552
§ 371 (c)(1), (2), (4) Date: Nov. 25, 2008

(87) PCT Pub. No.: WO2007/126152
PCT Pub. Date: Nov. 8, 2007

(65) Prior Publication Data
US 2009/0275048 A1 Nov. 5, 2009

(30) Foreign Application Priority Data
Apr. 28, 2006 (JP) ................ 2006-127047

(51) Int. Cl.
*C12P 21/08* (2006.01)
*C07K 16/18* (2006.01)
*C07K 16/44* (2006.01)
*G01N 33/53* (2006.01)

(52) U.S. Cl. ............ 530/388.1; 530/388.2; 435/7.1; 435/70.21; 435/810

(58) Field of Classification Search .................. None
See application file for complete search history.

(56) References Cited

U.S. PATENT DOCUMENTS 5,945,294 A * 8/1999 Frank et al. .......... 435/7.9
6,028,061 A 2/2000 Bernfield et al.

OTHER PUBLICATIONS

Dam et al, J Biol Chemistry 279(37): 38346-38352, Sep. 2004.*
Harlow et al, in Antibodies a Laboratory Manual, 1988, Cold Spring harbor laboratory publication, Cold Spring Harbor, NY, chapter 5, pp. 56-59, 72-81.*
Harlow et al, in Antibodies a Laboratory Manual, 1988, Cold Spring harbor laboratory publication, Cold Spring Harbor, NY, chapter 6, pp. 139-154.*
Joo, et al. "Nucleolin: Acharan Sulfate-binding Protein on the Surface of Cancer Cells," *Glycobiology*, vol. 15, No. 1, pp. 1-9, Jan. 2005.
Kim, et al. "A New Glycosaminoglycan from the Giant African Snail *Achatina fluica*," *The Journal of Biological Chemistry*, vol. 271, No. 20, pp. 11750-11755, May 17, 1996.
ten Dam, et al. "Detection of 2-*O*-Sulfated Iduronate and *N*-Acetylglucosamine Units in Heparan Sulfate by an Antibody Selected Against Acharan Sulfate (IdoA2S-GlcNAc)$_n$," *The Journal of Biological Chemistry*, vol. 279, No. 37, pp. 38346-38352, Sep. 10, 2004.

* cited by examiner

*Primary Examiner* — Phuong Huynh
(74) *Attorney, Agent, or Firm* — Knobbe, Martens, Olson & Bear, LLP

(57) ABSTRACT

An anti-acharan sulfate antibody, a hybridoma that produces the antibody, a detection method and a detection kit to which the antibody is applied are disclosed. The anti-acharan sulfate antibody can be produced by immunizing a mammal using as an antigen a substance obtained by chemically bonding a protein to acharan sulfate.

6 Claims, 4 Drawing Sheets

ANTI-ACHARAN SULFATE ANTIBODY AND ITS APPLICATION

CROSS-REFERENCE TO RELATED APPLICATIONS

This application is the U.S. National Phase under 35 U.S.C. §371 of International Application PCT/JP2007/059552, filed Apr. 27, 2007, which claims priority to JP 2006-127047, filed Apr. 28, 2006.

TECHNICAL FIELD

The present invention relates to an anti-acharan sulfate antibody and its application.

BACKGROUND ART

The abbreviations used in this application are as follows:
AS: acharan sulfate,
ACH: 2-O-desulfated AS,
GAG: glycosaminoglycan,
HA: hyaluronic acid,
CS: chondroitin sulfate,
NAH: N-acetylheparosan,
HEP: heparin,
HS: heparan sulfate,
EHS-HS: HS derived from murine Engelbreth-Holm-Swarm sarcoma,
$NH_2$-HEP: N-desulfated HEP,
NAc-HEP: N-desulfated/N-re-acetylated HEP,
6DSH: 6-O-desulfated HEP,
NAc-6DSH: N-acetylated 6DSH,
$NH_2$-6SH: (2-O/N)-desulfated HEP,
6SH: (2-O/N)-desulfated/N-re-acetylated HEP,
$NH_2$-2SH: (6-O/N)-desulfated HEP,
2SH: (6-O/N)-desulfated/N-re-acetylated HEP,
NSH: (2-O/6-O)-desulfated HEP,
$NH_2$-CDSH: completely desulfated HEP,
CDSH: completely desulfated/N-re-acetylated HEP,
Ch: chondroitin,
2DSH: 2-O-desulfated HEP,
NAC-NSH; N-acetylated NSH,
CS-A(W): whale-derived chondroitin sulfate A,
CS-A(S): shark-derived chondroitin sulfate A,
CS-B: chondroitin sulfate B,
CS-C: chondroitin sulfate C,
CS-D: chondroitin sulfate D,
CS-E: chondroitin sulfate E,
KLH: hemocyanin, and
BSA: bovine serum albumin.

AS is one type of GAG isolated from a giant east African land snail (scientific name: *Achatina fulica*). AS is a polysaccharide having a repeating structure of a disaccharide unit composed of N-acetylglucosamine and 2-O-sulfated iduronic acid (-[IdoA(2S)-GlcNAc]-) as a basic sugar chain structure, and known to have an extremely similar structure to that of HS and HEP (Non-patent document 1). As an antibody that reacts with AS, MW3G3 is known, however, an antibody that reacts with AS and does not react with heparan sulfate derived from bovine kidney has not been known (Non-patent document 2).

Non-patent document 1: Yon S. Kim et al., Journal of Biological Chemistry, Vol. 271, No. 20, pp. 11750-11755, 1996

Non-patent document 2: Gerdy B. ten Dam et al., Journal of Biological Chemistry, Vol. 279, pp. 38346-38352, 2004

DISCLOSURE OF THE INVENTION

An object of the present invention is to provide a novel anti-AS antibody, a hybridoma that produces the antibody, a detection method and a detection kit to which the antibody is applied.

The present inventors have made intensive studies in view of the above-mentioned object, and as a result they found an antibody that reacts with AS and does not react with HS derived from bovine kidney by using a substance obtained by chemically bonding a protein to AS as an antigen, thus the present invention has been completed. That is, the present invention is as follows.

(1) An antibody which reacts with AS and does not react with HS derived from bovine kidney (hereinafter referred to as an "antibody of the present invention").

(2) The antibody according to the above (1), which does not substantially react with HEP derived from porcine intestine.

(3) The antibody according to the above (1) or (2), which does not substantially react with EHS-HS.

(4) The antibody according to any one of the above (1) to (3), which does not substantially react with keratan sulfate derived from bovine cornea.

(5) The antibody according to any one of the above (1) to (4), which does not substantially react with HA.

(6) The antibody according to any one of the above (1) to (5), which does not substantially react with NAH.

(7) The antibody according to any one of the above (1) to (6), which is a monoclonal antibody.

(8) The antibody according to the above (7), which is a monoclonal antibody produced by a hybridoma formed by cell fusion of a lymphocyte derived from a mammal immunized using as an antigen a substance obtained by chemically bonding a protein to AS and a myeloma cell derived from a mammal.

(9) The antibody according to the above (8), wherein the lymphocyte and the myeloma cell are derived from a mouse.

(10) A monoclonal antibody produced by a hybridoma deposited at Patent Organism Depositary, National Institute of Advanced Industrial Science and Technology under the deposit number of FERM BP-10774, FERM BP-10775, FERM BP-10776, FERM BP-10777, FERM BP-10778.

(11) A substance, which is obtained by chemically bonding a protein to AS and has antigenicity capable of raising an antibody that reacts with AS (hereinafter referred to as an "antigen of the present invention").

(12) A hybridoma formed by cell fusion of a lymphocyte derived from a mammal immunized using as an antigen a substance obtained by chemically bonding a protein to AS and a myeloma cell derived from a mammal (hereinafter referred to as a "hybridoma of the present invention").

(13) The hybridoma according to the above (12), wherein the lymphocyte and the myeloma cell are derived from a mouse.

(14) A hybridoma deposited at Patent Organism Depositary, National Institute of Advanced Industrial Science and Technology under the deposit number of FERM BP-10774, FERM BP-10775, FERM BP-10776, FERM BP-10777, FERM BP-10778.

(15) A method for detecting AS present in a sample, characterized by comprising at least a step of bringing an antibody according to any one of the above (1) to (10) into contact with the sample (hereinafter referred to as a "detection method of the present invention").

(16) The detection method according to the above (15) wherein the sample is derived from a material selected from the group consisting of a body fluid, a cell, a tissue, and a culture of a cell or a microorganism.

(17) A kit for detecting AS present in a sample, comprising at least an antibody according to any one of the above (1) to (10) (hereinafter referred to as a "detection kit of the present invention").

(18) The detection kit according to the above (17), wherein the sample is derived from a material selected from the group consisting of a body fluid, a cell, a tissue and a culture of a cell or a microorganism.

Because of the reactivity with AS, the antibody of the present invention can be preferably used for detection of AS. In addition, by using the antigen of the present invention and the hybridoma of the present invention, the antibody of the present invention can be efficiently produced. Further, by the detection method of the present invention, AS present in a sample can be efficiently detected. Further, by using the detection kit of the present invention, detection of AS by the detection method of the present invention can be performed efficiently and conveniently.

BRIEF DESCRIPTION OF THE DRAWINGS

FIG. 4 is a graph showing the reactivities of AS17 antibody, AS22 antibody, AS25 antibody, AS38 antibody and AS48 antibody against various types of HEP derivatives and the like.

DESCRIPTION OF THE PREFERRED EMBODIMENTS

<1> Antibody of the Present Invention

Figure 1:
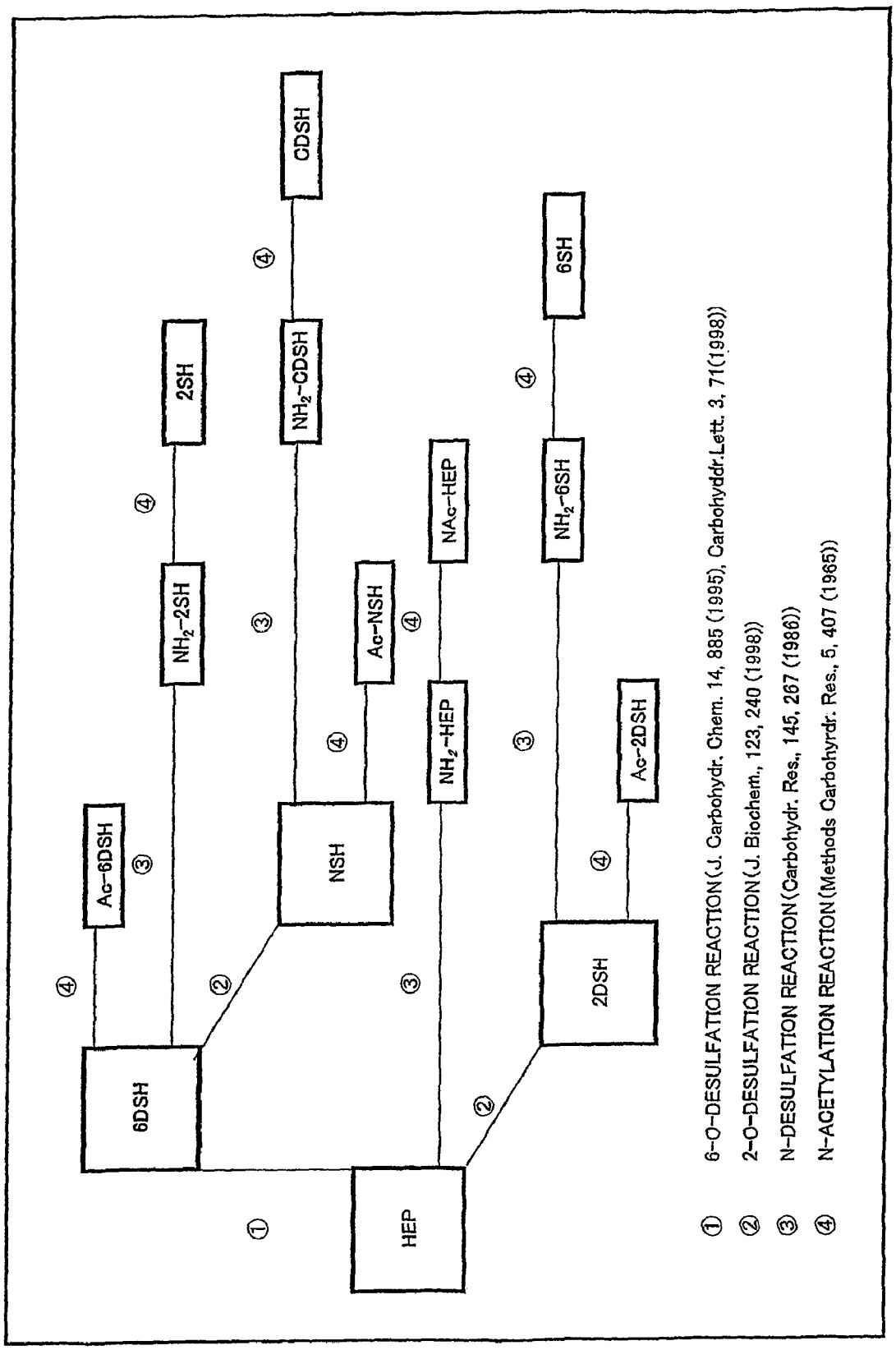
FIG. 1 is a view showing a flow of a method of producing various types of HEP derivatives.

An antibody of the present invention is an antibody that reacts with AS and does not substantially react with HS derived from bovine kidney.

AS is a polysaccharide having a repeating structure of a disaccharide unit composed of N-acetylglucosamine and 2-O-sulfated iduronic acid (-[IdoA(2S)-GlcNAc]-) as a basic sugar chain structure. AS can be prepared, for example, by a known method using a giant east African land snail (scientific name: *Achatina fulica*) as a raw material in the manner as described in the Examples shown below.

Further, in the above description, "reaction" means an immunological reaction or antigen-antibody reaction, and the reactivity can be determined by an ELISA method, an RIA method, a plaque assay, an agglutination reaction method, a flow cytometry method, a histological staining method, a Western blotting method or the like. For example, when an ELISA method is performed using an antibody at a specified concentration, in the case where a reaction signal is increased in proportion to an increase in the concentration of an antigen, it can be said that the antibody reacts with the antigen. In this specification, unless otherwise specified, the reactivity of the antibody of the present invention against an antigen means a relative reactivity when the reactivity of the antibody of the present invention against AS measured by a method described in the Example 5 shown below (antigen concentration: 0.1 μg/well) is determined to be 100%.

The phrase "does not substantially react" as used herein means that the degree of reactivity between an antibody and an antigen is a degree to which a reaction signal is not given when measurement is performed by a method described in the Example 5 shown below (antigen concentration: 0.1 μg/well), however, in this specification, it shall also be constructed to be a degree to which a reaction signal is not given when the degree to which a reactivity is, for example, about 5% or lower as compared with the reactivity against AS.

The antibody of the present invention is not particularly limited as long as it is an antibody that reacts with AS and does not substantially react with HS derived from bovine kidney, however, preferable antibodies include an antibody that does not substantially react with HEP derived from porcine intestine, an antibody that does not substantially react with EHS-HS, an antibody that does not substantially react with KS derived from bovine cornea, an antibody that does not substantially react with HA, and an antibody that does not substantially react with NAH. Among these antibodies, an antibody that reacts with AS and does not substantially react with HS derived from bovine kidney and HEP derived from porcine intestine is more preferred, and an antibody that reacts with AS and does not substantially react with any of HS derived from bovine kidney, HEP derived from porcine intestine, EHS-HS, KS derived from bovine cornea, HA and NAH is further more preferred. Further, an antibody that does not substantially react with any of CS-A(W), CS-A(S), CS-B, CS-C, CS-D, CS-E and Ch is also preferred.

Further, it is preferred that the antibody of the present invention does not substantially react with one or more HEP derivatives selected from the group consisting of: 6DSH, $NH_2$-6SH, 6SH, $NH_2$-2SH, NSH, NAc-NSH, $NH_2$-CDSH and CDSH.

As a preferred example of the reactivity of the antibody of the present invention against ACH, substantially no reactivity can be exemplified, and as another preferred example of the reactivity, 50 to 60% can be exemplified.

The reactivity of the antibody of the present invention against another HEP derivative is not particularly limited, however, the following reactivity can be exemplified.

As a preferred example of the reactivity of the antibody against NAc-HEP, 5 to 10% can be exemplified, and as another preferred example of the reactivity, 80 to 100% can be exemplified.

As a preferred example of the reactivity of the antibody against NAc-HEP, 3 to 15% can be exemplified, and as another preferred example of the reactivity, 80 to 100% can be exemplified.

As a preferred example of the reactivity of the antibody against NAc-6DSH, substantially no reactivity can be exemplified, and as another preferred example of the reactivity, 75 to 100% can be exemplified.

As a preferred example of the reactivity of the antibody against $NH_2$-2SH, substantially no reactivity can be exemplified, and as another preferred example of the reactivity, 15 to 25% can be exemplified.

As a preferred example of the reactivity of the antibody against 2SH, 20 to 40% can be exemplified, and as another preferred example of the reactivity, 70 to 80%, 90 to 110%, or 150 to 200% can be exemplified.

As a preferred example of the reactivity of the antibody against CDSH, substantially no reactivity can be exemplified, and as another preferred example of the reactivity, 15 to 25% can be exemplified.

The above-mentioned various types of GAG and various types of HEP derivatives are available or can be prepared by a method described in the Examples shown below.

An epitope of the antibody of the present invention is not particularly limited as long as it is a portion of AS, however, it preferably comprises the disaccharide unit composed of N-acetylglucosamine and 2-O-sulfated iduronic acid (-[IdoA (2S)-GlcNAc]-).

The antibody of the present invention may be either a monoclonal antibody or a polyclonal antibody, however, it is more preferably a monoclonal antibody. Further, the monoclonal antibody may be a fragment thereof. Examples of the fragment of the monoclonal antibody include F(ab')$_2$ antibodies, Fab antibodies, single chain antibodies (scFv), diabodies, minibodies and the like.

In the case where the antibody of the present invention is a monoclonal antibody, the antibody of the present invention can be produced, for example, by a hybridoma formed by cell fusion of a lymphocyte derived from a mammal immunized using as an antigen a substance obtained by chemically bonding a protein to AS and a myeloma cell derived from a mammal.

Further, in the case where the antibody of the present invention is a polyclonal antibody, the antibody of the present invention can be obtained, for example, from the serum of a mammal immunized using as an antigen a substance obtained by chemically bonding a protein to AS.

As the "protein" in the substance obtained by chemically bonding a protein to AS, for example, BSA and KLH can be exemplified, and, in particular, KLH is preferred.

Further, as the method of chemically bonding a protein to AS, a mode of the chemical bond is not particularly limited, however, a covalent bond is preferred, and a disulfide bond (hereinafter sometimes referred to as "-SS-") is more preferred. As the method of chemically bonding by a disulfide bond, for example, the following method can be adopted. That is, AS is reactive aminated and the resulting compound is reacted with 5 mM n-succinimidyl-3-(2-pyridyldithio)propionate(hereinafter referred to as "SPDP"), whereby 2-pyridyldithio propynylated AS is obtained. This compound is reduced with a reducing agent such as dithiothreitol, whereby thiolated AS is obtained. In this manner, a protein is reacted with SPDP, whereby a 2-pyridyldithio propynylated protein is obtained. Then, by mixing a solution of the thiolated GAG and a solution of the 2-pyridyldithio propynylated protein, a disulfide bond is formed between AS and the protein, whereby an AS-SS-protein is obtained.

An origin of the above-mentioned lymphocyte and myeloma cell is not particularly limited as long as they are derived from a mammal, and examples of the mammal include swine, cattle, mouse, rat and the like. In particular, mouse is preferred.

Further, in the above description, immunization can be carried out by subcutaneously injecting an antigen prepared by the above-mentioned method into a non-human mammal. The injection method is not limited to this, and it may be interperitoneal injection or intravenous injection. In general, immunization is performed several times, and, it is preferably performed by administration together with an adjuvant. As the adjuvant, those that can be expected to have an adjuvant effect such as alum, killed Mycobacterium tuberculosis, a nucleic acid, complete Freund's adjuvant or incomplete Freund's adjuvant may be used, however, Titer MAX Gold (manufactured by Sigma) is particularly preferred.

After the final immunization of a mouse is performed, the above-mentioned cell fusion can be carried out, for example, by a known method using a lymphocyte obtained from the lymph node or the spleen of the mouse and a cell of a tumor cell line such as a myeloma cell (generally, P3-NS-1/1-Ag4-1, P3-X63-Ag8-U1 (P3 U1), P3-X63-Ag8-653, SP2/0-Ag14 or the like derived from a BALB/c mouse).

Further, the above-mentioned hybridoma can be obtained, for example, by performing selection and cloning according to the following method. That is, a hybridoma that produces an antibody reacting with AS is selected from supernatant of a cell culture in which hybridomas grow well by various analysis methods (such as an RIA method, a plaque assay, an agglutination reaction method, an ELISA method, a flow cytometry method, a histological staining method and a Western blotting method), and then, cloning is performed for the obtained hybridoma. As the cloning method, FACS (fluorescent activated cell sorter), a limiting dilution method or the like which is generally used may be employed. For example, it is preferred that the limiting dilution method is performed in such a manner that the number of cells per well on a 96-well plate is not more than 1. Whatever methods are used, it is preferred that cloning is performed twice repeatedly so as to obtain a single clone.

By culturing the thus obtained single clone by an in vitro culture method, an in vivo culture (ascitic fluid) method or the like, a monoclonal antibody can be produced. The antibody can be separated and purified by appropriately combining general biochemical techniques such as salting out, ion exchange, gel filtration, affinity chromatography, electrophoresis and the like.

The immunoglobulin class of the antibody of the present invention and the subclass thereof are not particularly limited, however, it is preferred that the immunoglobulin class is IgM or IgG. In the case where the immunoglobulin class is IgG, it is more preferred that the subclass thereof is IgG2a or IgG1.

Specific examples of the antibody of the present invention include AS17 antibody, AS22 antibody, AS25 antibody, AS38 antibody and AS48 antibody, which are monoclonal antibodies produced by a hybridoma deposited at Patent Organism Depositary, National Institute of Advanced Industrial Science and Technology under the deposit number of FERM BP-10774, FERM BP-10775, FERM BP-10776, FERM BP-10777, FERM BP-10778 can be exemplified. Specific explanation will be made in the Examples shown below.

<2> Antigen of the Present Invention

The antigen of the present invention is a substance, which is obtained by chemically bonding a protein to AS and has antigenicity capable of raising an antibody that reacts with AS.

The explanation of the above-mentioned terms "protein" and "AS" and the method of chemically bonding the protein to AS is described in the above section <1> "antibody of the present invention". In addition, the above-mentioned "reaction" means an immunological reaction or an antigen-antibody reaction in the same manner as the case of the above section <1> "antibody of the present invention". The specific explanation is described in the above section <1> "antibody of the present invention".

Whether or not the antigen has antigenicity capable of raising an antibody that reacts with AS can be determined, for example, by immunizing a mammal using a substance obtained by chemically bonding a protein to AS by the method described in the above section <1> "antibody of the present invention" and confirming whether or not the antibody is present in a sample derived from the immunized mammal by an RIA method, a plaque assay, an agglutination reaction method, an ELISA method, a flow cytometry method, a histological staining method, a Western blotting method or the like.

The above-mentioned antibody that reacts with AS is preferably the antibody of the present invention. Therefore, the antigen of the present invention can be used for the purpose of producing the antibody of the present invention. In such a case, for example, as the antigen to be used for immunization described in <1> antibody of the present invention, the antigen of the present invention can be used. More specific explanation will be made in the Examples shown below.

<3> Hybridoma of the Present Invention

The hybridoma of the present invention is a hybridoma formed by cell fusion of a lymphocyte derived from a mammal immunized using as an antigen a substance obtained by chemically bonding a protein to AS and a myeloma cell derived from a mammal.

The explanation of the above-mentioned terms "protein" and "AS", the method of chemically bonding the protein to AS, "immunization", "a lymphocyte derived from a mammal", "a myeloma cell derived from a mammal", "cell fusion" and "hybridoma" is described in the above section <1> "antibody of the present invention".

Examples of the above-mentioned hybridoma of the present invention include hybridomas deposited at Patent Organism Depositary, National Institute of Advanced Industrial Science and Technology under the deposit number of FERM BP-10774, FERM BP-10775, FERM BP-10776, FERM BP-10777, or FERM BP-10778, respectively.

The hybridoma in the present invention can be used for producing the antibody of the present invention, especially for producing the monoclonal antibody of the present invention. For example, the antibody of the present invention can be produced, for example, by culturing the hybridoma of the present invention by an in vitro culture method, an in vivo culture (ascitic fluid) method or the like. The Examples described later describe more specific information.

<4> Detection Method of the Present Invention

The detection method of the present invention is a method for detecting AS present in a sample, characterized by comprising at least a step of bringing the antibody of the present invention into contact with the sample.

The above-mentioned "sample" is not particularly limited as long as it contains or may contain AS, and, the sample may be derived from a body fluid such as urine, blood, plasma, serum, synovial fluid or spinal fluid, a secreted substance, a cell such as an animal cell or a plant cell, a tissue, an organ, a culture of a cell or a microorganism (including, for example, a culture supernatant, etc.) or the like. The above-mentioned term "derived from" means that the sample may be a purified substance, an extracted substance or a specimen derived from any of the materials illustrated above, or may be as it is.

In the detection method of the present invention, as a specific method for detecting AS present in a sample, in the case where a tissue specimen is used as a sample, a standard immunohistological staining method or the like can be used, and in the case where a body fluid, a culture supernatant or the like is used as a sample, an ELISA method, an RIA method, a sandwich assay, a competitive assay, a plaque assay, an agglutination reaction method, a flow cytometry method, a Western blotting method or the like can be used.

In the above-mentioned sandwich assay, for example, the antibody of the present invention may be attached to a solid phase such as a plate and used as a primary antibody, or the antibody of the present invention may be labeled and used as a secondary antibody.

According to the detection method of the present invention, based on the reactivity of the antibody of the present invention with AS, AS present in a sample can be preferably detected. Further, the detection method of the present invention can be applied to AS-specific detection by utilizing the specific reactivity of the antibody of the present invention against various types of antigens described in <1> antibody of the present invention.

The detection in the detection method of the present invention may be either quantitative detection or qualitative detection. In the case of quantitative detection, the concentration of AS present in a sample can be determined, for example, by preparing a calibration curve for a relationship between the AS concentration and the detection results using AS standard solutions whose AS concentrations are known in advance and comparing a detection result for the sample in which the AS concentration is not known to the calibration curve.

<5> Detection Kit of the Present Invention

The detection kit of the present invention is a kit for detecting AS present in a sample, which contains at least the antibody of the present invention. With the use of the detection kit of the present invention, the detection method of the present invention can be carried out efficiently and conveniently. Examples of the "kit which contains at least the antibody of the present invention" as described in the above description include a kit containing the antibody of the present invention as it is (for example, a kit containing the antibody of the present invention dissolved in a solution, etc.), a kit containing a solid phase to which the antibody of the present invention has been attached, and a kit containing the antibody of the present invention labeled with an enzyme or the like. In addition, the above-mentioned term, "sample" means the same as described in the above section <4> "detection method of the present invention".

Further, the detection kit of the present invention may contain, in addition to the antibody of the present invention, for example, a primary antibody, a secondary antibody, a reaction buffer, a washing solution, a reaction substrate, an AS standard solution and the like.

EXAMPLES

Hereinafter, the present invention will be specifically described in more detail with reference to Examples.

Example 1

Reference Example 1

Preparation of AS and ACH

AS was prepared from a giant east African land snail (scientific name: *Achatina fulica*) according to the method of Kim, Y. S. et al. (J. Biol. Chem., 271, 11750 (1996)). By using the obtained AS as a raw material, ACH was prepared according to the method of Ishihara, M. et al. (J. Biochem., 121, 345 (1997)).

Reference Example 2

Preparation of 2-pyridyl Disulfide Propionylated KLH

The introduction of a 2-pyridyl disulfide structure into KLH was carried out according to the method of Carlsson, J. et al. (Biochem. J., 173, 723 (1978)).

More specifically, 60 mg of KLH (manufactured by Sigma) was dissolved in 0.1 M phosphate buffer (pH 7.5)/0.1 M NaCl to make a final concentration of 2.5 mg/ml. To this solution, 5 mM N-succinimidyl-3-[2-pyridylthio] propionic acid (hereinafter referred to as "SPDP" (manufactured by Sigma)) dissolved in ethanol was added and mixed to make a final concentration of 0.238 mM, and the mixture was maintained at room temperature for 30 minutes. After being dialyzed against distilled water to remove excess SPDP, the mixed solution was lyophilized, whereby 59.4 mg of 2-pyridyl disulfide propionylated KLH (hereinafter referred to as "PDP-KLH") was obtained.

Reference Example 3

Preparation of AS-BSA Conjugate Via Uronic Acid

Each of AS and BSA (manufactured by Bayer) was separately dissolved in 0.1 M MES buffer (pH 5.5) to make a final concentration of 10 mg/ml to obtain an AS solution and a BSA solution. The AS solution (300 µl) and the BSA solution (150 µl) were mixed and 400 µg of 1-(3-dimethylaminopropyl)-3-ethylcarbodiimide (hereinafter referred to as "EDC" (manufactured by PIERCE)) was added thereto, and then the mixture was maintained at room temperature for 20 hours with stirring. The resultant reaction solution was dialyzed overnight against distilled water and lyophilized, whereby 3.5 mg of AS-BSA conjugate via uronic acid was obtained.

Reference Example 4

Preparation of Biotin-Labeled GAG and Biotin-Labeled HEP Derivatives

For HA derived from porcine skin (hereinafter simply referred to as "HA"), CS-A (W), CS-A(S), CS-B, CS-C, CS-D, CS-E, HS derived from bovine kidney (hereinafter simply referred to as "HS"), and KS derived from bovine cornea (hereinafter simply referred to as "KS"), those manufactured by Seikagaku Corporation were used. NAH was prepared from a culture of $E.$ $coli$ K5 according to the method described in JP-A-2004-18840. HEP derived from porcine intestine (hereinafter simply referred to as "HEP" in Examples) was purchased from Scientific Protein Laboratories. EHS-HS was prepared according to the method described in JP-B-7-53756.

Various types of HEP derivatives ($NH_2$-HEP, NAC-HEP, 6DSH, NAc-6DSH, $NH_2$-6SH, 6SH, $NH_2$-2SH, 2SH, NSH, NAC-NSH, $NH_2$-CDSH and CDSH) were prepared according to the method shown in FIG. 1. In FIG. 1, 6-O-, 2-O- and N-desulfation of HEP were carried out according to the methods of Takano et al., Kariya et al., and Ayotte, L. et al., respectively (Takano, R. et al., J. Carbohydr. Chem. 14, 885 (1995), Takano, R. et al., Carbohydr. Lett. 3, 71 (1998), Kariya, Y. et al., J. Biochem., 123, 240 (1998), and Ayotte, L. et al., Carbohydr. Res., 145, 267 (1986)).

N-acetylation was carried out according to the method of Danishefsky, I. et al. (Danishefsky, I. et al., Methods Carbohydr. Res., 5, 407 (1965)).

Because N-desulfation also occurs as a side reaction in some degree when 6-O-desulfation is carried out according to the method of Takano et al., part of the obtained 6DSH and NSH was subjected to N-acetylation to prepare NAc-6DSH and NAc-NSH.

Each of the above-mentioned various types of GAG and various types of HEP derivatives and AS and ACH prepared in Reference example 1 was separately dissolved in 0.1 M MES buffer (pH 5.5) to make a final concentration of 10 mg/ml and thereby, various types of GAG solutions and various types of HEP derivative solutions were obtained. To 1 ml of each of these various types of GAG solutions and various types of HEP derivative solutions, 25 µl of biotin-LC-hydrazide (manufactured by PIERCE) adjusted to be 20 mM with dimethylsulfoxide (manufactured by Wako Pure Chemical Industries) was added. Then, 12.5 µl of EDC solution adjusted to be 100 mg/ml with 0.1 MMES buffer (pH 5.5) was added thereto. After being mixed well, the mixed solution was allowed to react at room temperature (15° C. to 25° C.) for 20 hours with stirring. The resultant reaction product was subjected to dialysis using a dialysis membrane (cutoff; molecular weight 10,000 or smaller) against Dulbecco's phosphate buffered saline (pH 7.2 to 7.5, not containing divalent ions such as calcium ion, hereinafter referred to as "PBS(−)") to remove free biotin sufficiently, whereby various types of biotin-labeled GAG (hereinafter referred to as "Bi-GAG") and various types of biotin-labeled HEP derivatives (hereinafter referred to as "Bi-HEP derivatives") were obtained. After the dialysis, the concentration of Bi-GAG or Bi-HEP derivatives was adjusted to 5 mg/ml and cryopreserved.

Hereinafter, biotin-labeled AS is referred to as "Bi-AS".

Reference Example 5

Preparation of Streptavidin-Coated Microplate

Streptavidin (manufactured by Vector Laboratories) was diluted with PBS(−) to 20 µg/ml and 50 µl of this solution was added to each well of a Maxisorp (registered trademark) 96-well microplate (manufactured by Nunc). The plate was uniformly coated with streptavidin by storing it for 18 hours at 4° C., and then washed twice with PBS(−). Subsequently, by using AppileDuo (registered trademark, manufactured by Seikagaku Corporation) as a blocking agent, areas that were not coated with streptavidin were blocked according to the following method. That is, AppileDuo (registered trademark) (hereinafter referred to as a "blocking solution") was diluted 5-fold by using a phosphate buffer containing 0.05% Proclin 300 (registered trademark, manufactured by SUPELCO) as an antiseptic agent (pH 7.2 to 7.5, hereinafter referred to as "PB"), and 250 µl of this blocking solution was added to each well and the plate was let stand at room temperature for 2 hours. Thereafter, the blocking solution was removed sufficiently and the plate was dried at 37° C. for 2 hours, whereby a streptavidin-coated microplate was obtained. The obtained plate was enclosed in an aluminum-laminated bag with a desiccant and stored under refrigeration.

Reference Example 6

Preparation of Microplates Coated With Various Types of GAG and Microplates Coated With Various Types of HEP Derivatives 1) Preparation of AS-Coated Microplate The AS-BSA conjugate (50 ng) prepared in Reference example 3 was added to a Maxisorp (registered trademark)

96-well microplate and the plate was maintained for 18 hours at 4° C. Then, blocking was carried out using Block Ace (registered trademark, manufactured by Dainippon Pharmaceutical Co., Ltd.) diluted 4-fold with PBS(−) containing 0.05% Proclin 300 (registered trademark) as an antiseptic agent. After the plate was let stand for 1 hour at room temperature, an AS-coated microplate was obtained. This AS-coated microplate was used to verify an antibody titer in the serum in the Example 3 shown below.

2) Preparation of Microplates Coated With Various Types of Bi-GAG and Microplates Coated With Various Types of Bi-HEP Derivatives Each of various types of Bi-GAG and various types of Bi-HEP derivatives described in the above-mentioned Reference example 4 was separately dissolved in an AppliéDuo (registered trademark) solution diluted 20-fold with PBS(−) containing 0.05% Proclin 300 (registered trademark) to make a final concentration of 1 μg/ml (hereinafter these solutions are referred to as "various types of Bi-GAG solutions" and "various types of Bi-HEP derivative solutions"). Each well of the streptavidin-coated microplate prepared in Reference example 5 was washed 4 times with 300 μl of PBS(−) containing 0.05% Proclin 300 (registered trademark) and 0.05% polyoxyethylene (20) sorbitan monolaurate (hereinafter referred to as a "washing buffer"). In each well, 100 μl of each of the various types of Bi-GAG solutions and various types of Bi-HEP derivative solutions was dispensed, and the plate was let stand for 30 minutes at room temperature. Then, each well was washed 4 times with the washing buffer, whereby microplates coated with various types of Bi-GAG and microplates coated with various types of Bi-HEP derivatives were obtained. These microplates were used for cloning in the Example 3 shown below and a reactivity test in the Example 5 shown below.

Example 2

Preparation of AS Antigen

1) Preparation of Reductive Aminated AS

Four milligrams of AS prepared in Reference example 1 in Example 1 was weighed and dissolved in 160 μl of 2 M aqueous ammonium chloride solution. To this solution, 12 mg of sodium cyanohydridoborate was added and reductive amination reaction was carried out at 70° C. for 2 days. To the resultant reaction solution, 5 mg of sodium cyanohydridoborate was added and the reaction was carried out under the same conditions as described above for an additional 2 days. The obtained solution was cooled in an ice bath and the reaction was completely terminated by adding 32 μl of acetic acid. By a solvent precipitation method using two volumes of ethanol, reductive aminated AS (hereinafter referred to as "RA-AS") was recovered. The obtained precipitate was washed with ethanol and then lyophilized, whereby 3.3 mg of lyophilized RA-AS was obtained.

2) Preparation of 2-pyridyl Disulfide Propionylated AS

Three point three milligrams of RA-AS prepared in the above 1) was dissolved in 1 ml of 0.1 M sodium chloride/0.1 M phosphate buffer (pH 7.5). After 80 μl of 5 mM SPDP ethanol solution was added to this solution, the mixture was let stand overnight at room temperature to allow a 2-pyridyl disulfide propionylation reaction (PDP reaction) to proceed. After dialysis was carried out using distilled water to remove excess SPDP, followed by lyophilization, whereby 3.8 mg of lyophilized 2-pyridyl disulfide propionylated AS (hereinafter referred to as "PDP-AS") was obtained.

3) Preparation of Thiopropionyl AS

Two point zero milligrams of PDP-AS prepared in the above 2) was weighed and dissolved in 160 μl of 0.1 M sodium chloride/0.1 M sodium acetate buffer (pH 4.5). To this solution, dithiothreitol was added to make a final concentration of 25 mM and a reductive reaction was carried out for 60 minutes at room temperature. By a solvent precipitation method using two volumes of ethanol, thiopropionyl AS (hereinafter referred to as "SH-AS") was recovered. The obtained precipitate was washed with ethanol and then lyophilized, whereby 1.5 mg of lyophilized SH-AS was obtained.

4) Preparation of AS-KLH Conjugate Via Disulfide Bond

One point five milligrams of SH-AS prepared in the above 3) and 0.75 mg of PDP-KLH prepared in Reference example 2 were dissolved in 1 ml of 0.1 M sodium chloride/0.1 M phosphate buffer (pH 7.5) and a conjugation reaction was carried out for 2 hours at room temperature. The resultant reaction solution was dialyzed overnight against distilled water to remove pyridyl-2-thione generated during the reaction, followed by lyophilization, whereby 1.9 mg of lyophilized AS-KLH conjugate was obtained. The obtained lyophilized product was used as an AS antigen in the following Example 3.

Example 3

Establishment of a Hybridoma Cell Line Producing an Antibody That Reacts With AS 1) Immunization of a Mouse One milligram of the AS antigen was dissolved in a small amount of distilled water, and the solution was mixed with 2 ml of Titer MAX Gold (registered trademark, manufactured by Sigma), whereby an antigen solution was prepared. As animals for immunization, 4 BALB/C mice (6 weeks of age, female, produced by Charles River Japan, Inc.) were used. The above-mentioned antigen solution was subcutaneously administered every two weeks at 100 μl/animal for two or three times. When the antibody titer in the serum reached a sufficient level, 100 μl/animal of an AS antigen solution without an adjuvant was administered as final immunization. Three days after the final immunization, the immunized mice were euthanized and the spleen was excised. In the above description, the verification of the antibody titer in the serum was carried out according to the following method. That is, by using the AS-coated microplate prepared in 1) in Reference example 6 and an alkaline phosphatase-labeled anti-mouse IgG+M+A (hereinafter referred to as "ALP anti-mouse Ig"), the antibody titer in the serum was verified by an enzyme-linked immunosorbent assay (ELISA). That is, 50 μl of the serum was dispensed in the AS-coated microplate and the plate was incubated at 37° C. for 1 hour. Subsequently, the plate was washed 4 times with PBS(−), and then 50 μl of an ALP anti-mouse Ig solution diluted 1000-fold with 10% BlockAce (registered trademark)/PBS(−) was dispensed in each well. After the plate was washed 4 times with PBS(−), 50 μl of a substrate solution (ALP rose, manufactured by Shino-Test Corporation) was dispensed in each well and the plate was let stand for 20 minutes at room temperature. Then, 50 μl of a coloring reagent (manufactured by Shino-Test Corporation) was added thereto and an absorbance at 495 nm was measured using 660 nm as background correction.

2) Establishment of a Hybridoma

Immunosensitized lymphocytes were collected from the spleen excised in 1) and mixed with mouse myeloma P3U1 cells (manufactured by SHIMA Laboratories Co., Ltd.) at a ratio of 4.4:1 to 5:1, and cell fusion was carried out by cocentrifugation in 50% polyethylene glycol 1500 (manufactured by Roche). As the myeloma cells to be used in the above cell fusion, the cells grown in an HAT medium containing 8-azaguanine for 1 week prior to the cell fusion were used. After the cell fusion, cells grown in the HAT medium were used in the following clone selection.

3) Selection and Evaluation of Clone 3-1) Cloning

A limiting dilution method was used for cloning. That is, cells were diluted with the HAT medium in such a manner that the number of cells per well was not more than 1, and dispensed into a 96-well microplate. The plate was incubated according to a standard method to obtain a culture supernatant. The evaluation of the antibody titer of the culture supernatant was carried out by an ELISA method using the Bi-AS-coated microplate prepared in 2) in Reference example 6 and a clone having reactivity was selected. The above-mentioned cloning procedure was conducted at least twice. As a result, 6 clones were selected.

3-2) Evaluation of Clone

To confirm that the reactivity of each of the antibody produced from the clones obtained in the above 3-1) was maintained, the clones were cultured in a 24-well plate, respectively, and the evaluation of the antibody titer of each of the obtained culture supernatants was carried out by an ELISA method using the Bi-AS-coated microplate prepared in 2) in Reference example 6 and a horseradish peroxidase-labeled goat anti-mouse immunoglobulin (hereinafter referred to as "HRP anti-mouse Ig", manufactured by DAKO). The details are as follows.

[Evaluation of Antibody Titer of the Clone]

In the Bi-AS-coated microplate washed 4 times with the washing buffer in advance, 100 µl of the culture supernatant was dispensed and the plate was let stand at room temperature for 1 hour. After the plate was further washed 4 times with the washing buffer, 100 µl of the HRP anti-mouse Ig, which was diluted 2000-fold with a reaction buffer (ApplieDuo (registered trademark) solution diluted 20-fold with PBS(−) containing 0.05% Proclin 300 (registered trademark)), was dispensed in each well. After being let stand at room temperature for 1 hour, this plate was washed 4 times with the washing buffer and then, 100 µl of a tetramethyl benzidine solution (an HRP substrate solution, manufactured by BIOFX Laboratories, Inc.) was added to each well and an enzyme reaction was carried out for 30 minutes at 37° C. After the reaction, 100 µl of a coloring reagent (manufactured by BIOFX Laboratories, Inc.) was added to each well and an absorbance at 450 nm was measured using 630 nm as background correction. The reaction buffer was used as a negative blank. As a result, it was confirmed that each clone produces an anti-AS antibody. Because the clone numbers of the established hybridomas were AS17, AS22, AS25, AS38 and AS48, the antibodies produced by these hybridomas were named AS17 antibody, AS22 antibody, AS25 antibody, AS38 antibody and AS48 antibody, respectively. The hybridomas were deposited at Patent Organism Depositary, National Institute of Advanced Industrial Science and Technology (AIST, Tsukuba Central 6, 1-1, Higashi 1-Chome, Tsukuba-shi, Ibaraki-ken, 305-8566, Japan) on Mar. 1, 2006 and the deposition numbers of FERM P-20823, FERM P-20824, FERM P-20825, FERM P-20826, FERM P-20827 were given, respectively. Then, they were converted into international deposits under the Budapest Treaty and received accession numbers FERM BP-10774, FERM BP-10775, FERM BP-10776, FERM BP-10777, FERM BP-10778, respectively. The immunoglobulin classes of the antibodies and their subclasses were examined according to a standard method, and as a result, it was found that AS17 antibody was classified into IgG2a, AS25 antibody and AS38 antibody were classified into IgG1, and AS22 antibody and AS48 antibody were classified into IgM.

Example 4

Preparation of an Anti-AS Monoclonal Antibody

1) Production of an Anti-AS Monoclonal Antibody

As the method of producing an anti-AS monoclonal antibody, a mouse ascitic fluid method was used. That is, $5 \times 10^6$ cells of each of the hybridomas (AS17, AS22, AS25, AS38 and AS48) established in the above 3) in Example 3 were injected into the abdominal cavity of a BALB/C mouse (15 weeks of age, female) which was treated with pristane (2,6,10,14-tetramethylpentadecane, Tokyo Chemical Industry Co., Ltd) in advance. During 10 to 20 days after the injection, the ascitic fluid of the mouse was collected several times separately and about 10 ml of ascetic fluid in total was obtained for each hybridoma.

2) Purification of the Anti-AS Monoclonal Antibody

The purification method for the IgG type antibodies (AS17 antibody, AS25 antibody and AS38 antibody) is shown below. That is, each of the ascitic fluids obtained in the above 1) was dialyzed overnight against adsorption buffer 1 (20 mM phosphate buffer (pH 7.0)). Each of the dialysate was filtered with a membrane filter (pore size: 0.45 nm), and the obtained filtrates were applied to HiTrap Protein G HP columns (5 ml, manufactured by Amersham Biosciences) equilibrated with the adsorption buffer 1 in advance, and then the columns were washed with the adsorption buffer 1. When the absorption at 280 nm of the respective solutions passing through the columns became almost 0, 0.1 M glycine buffer (pH 2.7) was applied to the columns to elute AS17 antibody, AS25 antibody and AS38 antibody, respectively. The solutions containing the respective antibodies were collected, respectively, and sufficiently dialyzed against PBS(−). The dialysates were appropriately adjusted to a proper concentration by such as concentration by ultrafiltration as needed, and the resulting solutions were used as purified antibodies. The amounts of the purified AS17 antibody, AS25 antibody and AS38 antibody were 30.8 mg, 4.6 mg and 11.5 mg, respectively.

The purification method for the IgM type antibodies (AS22 antibody and AS48 antibody) is shown below. That is, each of the ascitic fluids obtained in the above 1) was dialyzed overnight against adsorption buffer 2 (20 mM phosphate buffer (pH 7.5) containing 0.5 M $K_2SO_4$), respectively. The dialysates were filtered with a membrane filter (pore size: 0.45 nm), and the obtained filtrates were applied to HiTrap IgY Purification HP columns (5 ml, manufactured by Amersham Biosciences) equilibrated with the adsorption buffer 1 in advance, and then the columns were washed with the adsorption buffer 1. When the absorption at 280 nm of the respective solutions passing through the columns became almost 0, 20 mM phosphate buffer (pH 7.5) was applied to the columns to elute AS22 antibody and AS48 antibody, respectively. Then, by performing salting out (($NH_4)_2SO_4$: 50% saturation), the eluted AS22 antibody and AS48 antibody were recovered. The obtained precipitates were dialyzed against PBS(−) and the obtained dialysates were used as purified antibodies. The amounts of the purified AS22 antibody and AS48 antibody were 2.7 mg and 2.2 mg, respectively.

Example 5

Reactivity Test for Respective Purified Antibodies

The reactivities of the respective purified antibodies against various types of GAG and various types of HEP derivatives were verified.

1) Reactivity Test for Respective Purified Antibodies
Part 1) Reactivity Test Against AS
1)-1 Method Bi-AS-coated microplates were prepared in the same manner as in 2) in Reference example 6 except that the final concentration of Bi-AS in a Bi-AS solution used for coating was changed to 0.001, 0.004, 0.012, 0.037, 0.111, 0.333 or 1.000 µg/ml. The microplates were washed 4 times with the washing buffer, and then, 100 µl of each test solution, which contains each purified antibody diluted to be 0.025 mg/ml (AS17 antibody), 0.07 mg/ml (AS22 antibody), 0.006 mg/ml (AS25 antibody), 0.006 mg/ml (AS38 antibody) or 0.1 mg/ml (AS48 antibody) with PBS(−) containing AppliEduo (registered trademark, a final dilution of 20-fold, manufactured by Seikagaku Corporation) as an additive and 0.05% Proclin 300 as an antiseptic agent (hereinafter referred to as "reaction solution A"), was added to each well, and the plate was let stand at room temperature for 60 minutes to allow an antigen-antibody reaction to proceed. After the reaction, each well was washed 4 times with the washing buffer and then, 100 µl of a solution of a horseradish peroxidase-labeled goat anti-mouse immunoglobulin antibody (manufactured by Dako) obtained by diluting the antibody 2000-fold with the reaction solution A was added to each well as a secondary antibody solution and the plate was let stand at room temperature for 60 minutes to allow an antigen-antibody reaction to proceed. After the reaction, this plate was washed 4 times with the washing buffer and then, 100 µl of a tetramethyl benzidine solution (hereinafter referred to as "TMB solution", manufactured by BIOFX Laboratories, Inc.) as a substrate for peroxidase was added to each well, and the reaction was allowed to proceed at room temperature for 30 minutes for developing color. Then, 100 µl of a reaction termination solution (manufactured by BIOFX Laboratories, Inc.) was added to the plate for terminating the reaction, and an absorbance at a wavelength of 450 nm (a reference wavelength of 630 nm) that increases with TMB decomposition was measured with a Well Reader SK-603 (registered trademark, distributed by Seikagaku Corporation). The reactivities of the antibodies were evaluated based on an absorbance difference obtained by subtracting the absorbance in a well containing the reaction solution A (blank) as a test solution from the absorbance in a well containing each of the purified antibody solutions as a test solution (hereinafter referred to as an "absorbance difference").

1)-2 Results

Figure 2:
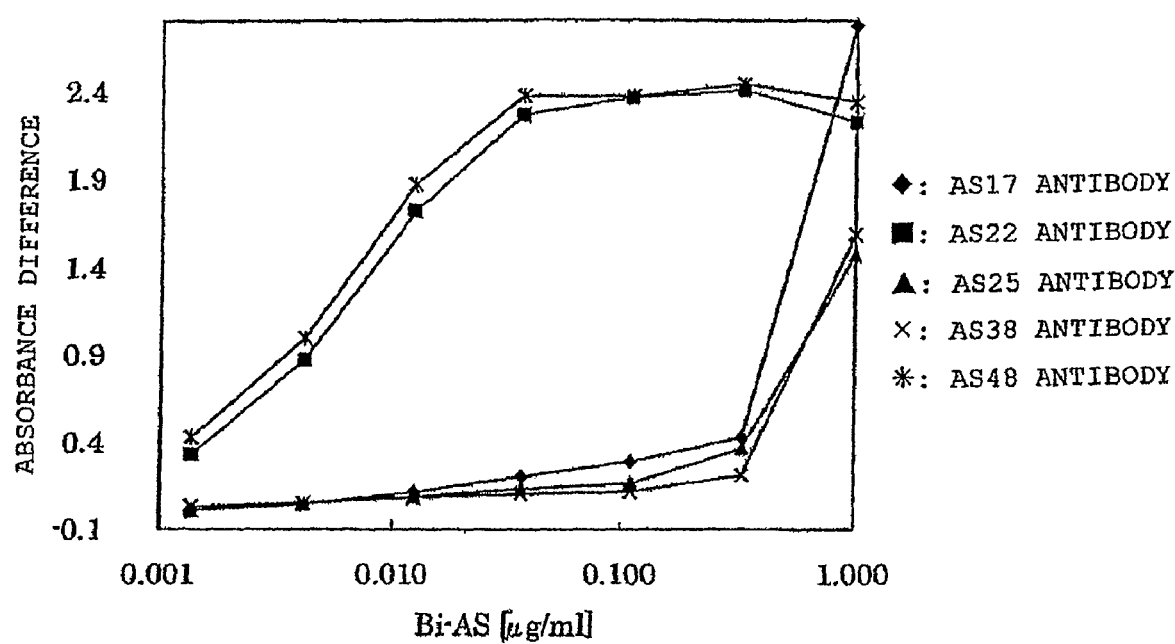
FIG. 2 is a graph showing the reactivities of AS17 antibody, AS22 antibody, AS25 antibody, AS38 antibody and AS48 antibody against AS. Bi-AS (μg/ml) on the horizontal axis indicates the final concentration of Bi-AS in a Bi-AS solution used for preparing a Bi-AS-coated plate.

The results are shown in FIG. 2. The relative sensitivities of AS22 antibody and AS48 antibody against AS are 100-fold stronger than those of AS17 antibody, AS25 antibody and AS38 antibody. When the concentration of Bi-AS is 1.0 µg/ml (0.1 µg/well), all the antibodies showed strong reactivity (absorbance difference ≧ 1).

2) Reactivity Test for Respective Purified Antibodies
Part 2) Reactivity Test Against Various Types of GAG
2)-1 Method The reactivities of the respective purified antibodies against various types of GAG were evaluated in the same manner as in the above 1)-1 except that the concentration of various types of Bi-GAG to be used is fixed at 1.0 µg/ml (0.1 µg/well)

2)-2 Results

Figure 3:
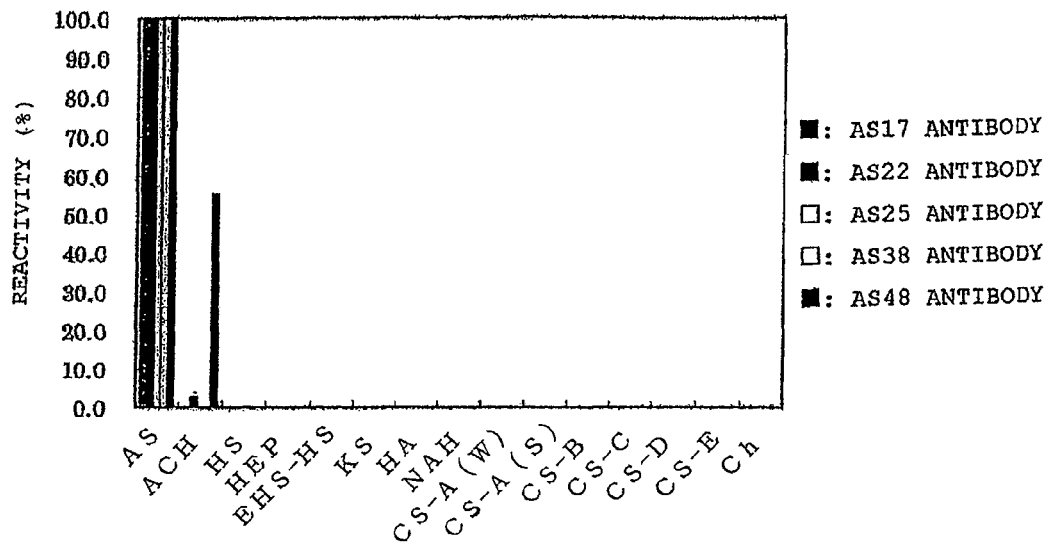
FIG. 3 is a graph showing the reactivities of AS17 antibody, AS22 antibody, AS25 antibody, AS38 antibody and AS48 antibody against various types of GAG.

The results of reactivities of the respective purified antibodies against various types of GAG are shown in FIG. 3.

All of the antibodies strongly reacted with AS in the same manner as in the above 1). Further, it was confirmed that any of the antibodies did not react with HS or HEP. Further, it was confirmed that AS17 antibody, AS22 antibody, AS25 antibody and AS38 antibody did not substantially react with any of the other GAG, i.e., ACH, EHS-HS, KS, HA, NAH, CS-A(W), CS-A(S), CS-B, CS-C, CS-D, CS-E and Ch. On the other hand, it was confirmed that AS48 antibody did not react with any of EHS-HS, KS, HA, NAH, CS-A(W), CS-A(S), CS-B, CS-C, CS-D, CS-E and Ch, however, it has a reactivity of about 55% against ACH.

From these results, it was indicated that a 2-O-sulfated iduronic acid (IdoA(2S)) residue is included in the epitope of any of these antibodies. Further, it was inferred that because most of the α(1-4) linkage of IdoA(2S) exist as a disaccharide unit linked to sulfaminoglucosamine (hereinafter referred to as "GlcNS") or O-sulfated GlcNS in the molecule of HS and HEP, with which any of the antibodies did not show the reactivities, modification of the glucosamine residues in HS and HEP may also be a negative factor for the reaction of these antibodies.

Figure 4:
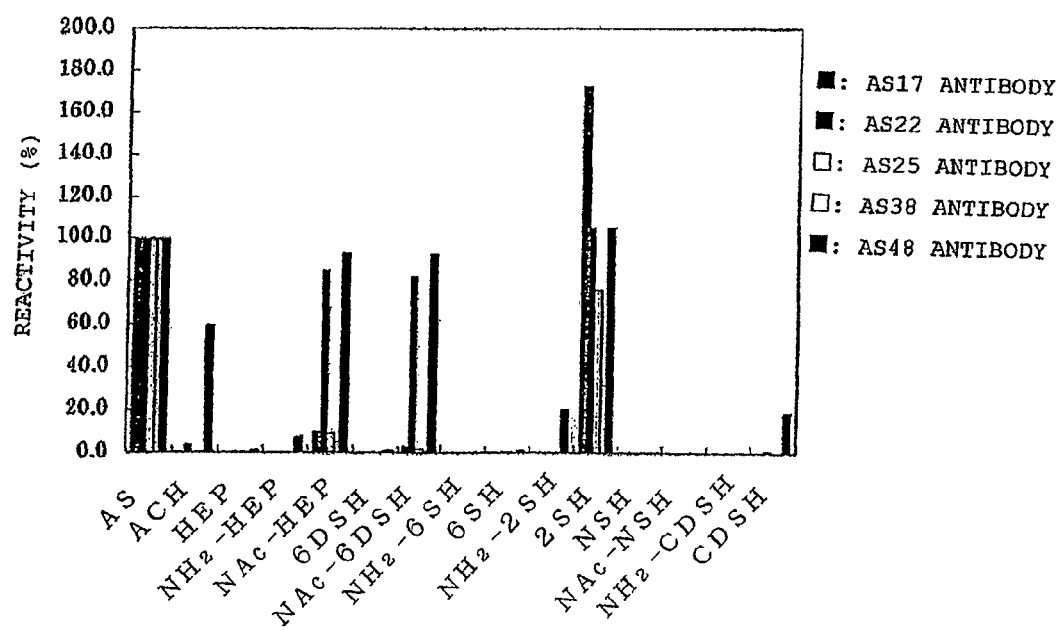

3) Reactivity Test for Respective Purified Antibodies
Part 3) Reactivity Test Against Various Types of HEP Derivatives To confirm the necessity of N-acetylation of the glucosamine residues for the reaction of the respective antibodies against an antigen, the reactivities were evaluated in the same manner as in the above 2)-1 except that the plates coated with various types of Bi-HEP derivatives described in Reference example 6 in Example 1 were used. The results are shown in FIG. 4.

All of the antibodies reacted with 2SH. The reactivities of AS17 antibody, AS22 antibody, AS25 antibody, AS38 antibody and AS48 antibody were 172.2%, 104.9%, 76.4%, 31.7% and 104.8%, respectively. 2SH is composed of an N-acetylglucosamine unit (-[GlcA-GlcNAc]-) and a 2-O-sulfated iduronic acid unit (-[IdoA(2S)-GlcNAc]-) and the existing ratio of the 2-O-sulfated iduronic acid unit is high (60% or more). Therefore, there is no discrepancy between the results of the above 1) and 2). On the other hand, AS17 antibody, AS22 antibody, AS25 antibody and AS38 antibody did not react with $NH_2$-2SH. Therefore, from these results, it was indicated that an N-acetylated glucosamine residue is included in the epitopes of AS17 antibody, AS22 antibody, AS25 antibody and AS38 antibody. Further, AS22 antibody and AS48 antibody reacted with NAC-HEP and NAc-6DSH, but did not react with $NH_2$-HEP or 6DSH. From these results, it was indicated that a glucosamine residue subjected to some modification (N-acetylation or N-sulfation) is also included in the epitopes of AS22 antibody and AS48 antibody.

Example 6

Histological Staining

Immunohistological staining was performed using a frozen section of rat cerebellum.

An SD rat (produced by Charles River Japan, Inc., 8 weeks of age, male) was anesthetized with diethyl ether (manufactured by Wako Pure Chemical Industries) and killed by exsanguination via the abdominal aorta, and then the cerebellum was excised. The excised cerebellum was embedded into OCT compound (manufactured by Sankyo Miles) and frozen with acetone/dry ice and a section of 6 µm in thickness was prepared using a Cryostat (distributed by Leica).

After the prepared section was air-dried for 2 hours at room temperature, it was fixed using chilled acetone (4° C.) and further air-dried at room temperature for an additional 1 hour. Then, the section was washed with PBS(−) containing 0.1% BSA and soaked in distilled water containing 0.1% sodium azide (manufactured by Wako Pure Chemical Industries) and 0.3% hydrogen peroxide solution (manufactured by Wako Pure Chemical Industries) at room temperature for 10 minutes, whereby an endogenous peroxidase activity was quenched. Then, the section was washed with PBS(−) containing 0.1% BSA and then, blocking was carried out with PBS(−) containing 0.1% BSA and 0.1% casein (manufactured by Wako Pure Chemical Industries) at room temperature for 60 minutes.

Then, the section was washed with PBS(−) containing 0.1% BSA, and the blocking of endogenous biotin was carried out using an Avidin-biotin blocking kit (manufactured by VECTOR Laboratories).

Thereafter, the section was washed with PBS(−) containing 0.1% BSA, and then, AS25 antibody diluted to 1 µg/ml with PBS(−) containing 0.1% BSA and 0.1% casein was reacted overnight at 4° C. After the section was washed with PBS(−) containing 0.1% BSA, biotin-labeled anti-mouse IgG+IgM (manufactured by JACKSON) containing 10% rat serum, which was diluted 500-fold with PBS, was reacted at room temperature for 30 minutes. After the section was washed with PBS(−) containing 0.1% BSA, peroxidase-labeled streptavidin (manufactured by NICHIREI CORPORATION) was reacted at room temperature for 30 minutes. After the section was washed with PBS(−) containing 0.1% BSA, a brown color development reaction was carried out using a DAB color development kit (manufactured by ZYMED LABORATORIES).

After the color development, the reaction was terminated by soaking the section in PBS(−) containing 0.1% BSA and the section was washed with water for 5 minutes. Thereafter, nuclear staining (blue) was carried out using hematoxylin (manufactured by DAKO) for contrast staining. After the section was washed with water for 5 minutes, dehydration and penetration treatment were carried out for embedding according to a standard method.

Figure 5:
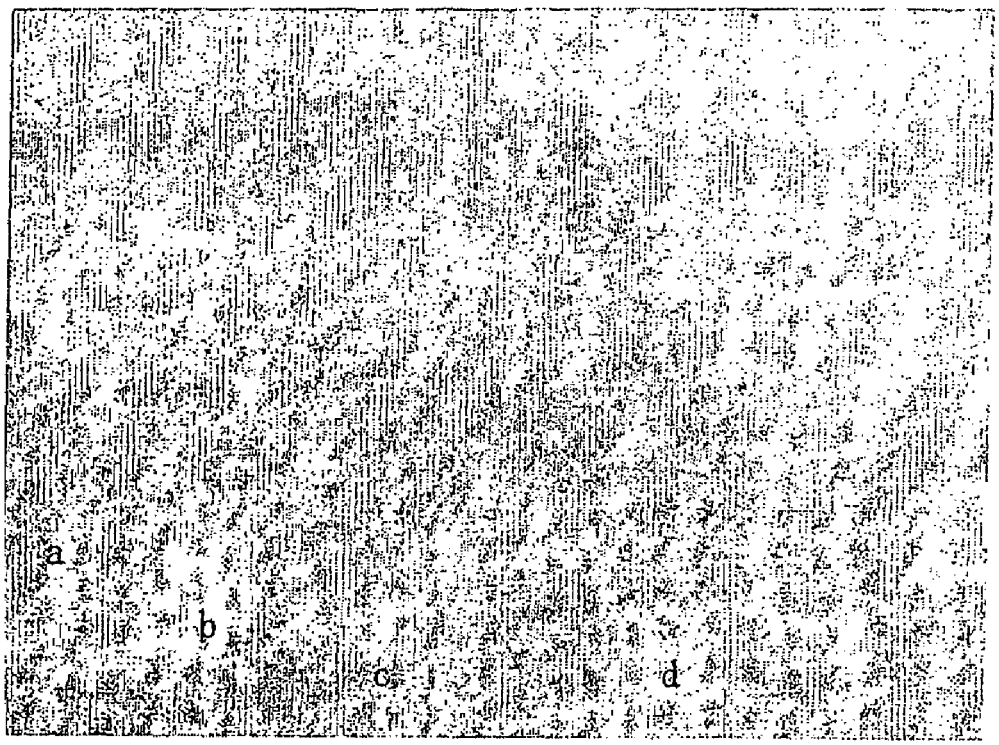
FIG. 5 is an image (photograph) showing the result of histological staining of rat cerebellum using AS25 antibody. a: MOLECULAR LAYER, b: PURKINJE CELL LAYER, c: GRANULAR LAYER, d: WHITE MATTER

The obtained staining image is shown in FIG. 5. Positive signals were observed in the molecular layer (a).

INDUSTRIAL APPLICABILITY

The antibody of the present invention is very useful because it can be preferably used for detecting AS. In addition, the antigen of the present invention and the hybridoma of the present invention are very useful because they can be used for efficiently producing the antibody of the present invention. Further, according to the detection method of the present invention, AS can be efficiently detected, therefore, the method is very useful. Further, the detection kit of the present invention is very useful because by using this kit, the detection method of the present invention can be more efficiently and conveniently performed.

What is claimed is:

1. A monoclonal antibody produced by a hybridoma deposited at Patent Organism Depositary, National Institute of Advanced Industrial Science and Technology under the deposit number of FERM BP-10774, FERM BP-10775, FERM BP-10776, FERM BP-10777, or FERM BP-10778.

2. A hybridoma deposited at Patent Organism Depositary, National Institute of Advanced Industrial Science and Technology under the deposit number of FERM BP-10774, FERM BP-10775, FERM BP-10776, FERM BP-10777, or FERM BP-10778.

3. A method for detecting acharan sulfate present in a sample, comprising contacting the sample with one of the antibodies according to claim 1 and detecting the present of acharan sulfate in the sample.

4. The detection method according to claim 3, wherein the sample is selected from the group consisting of a body fluid, a cell, a tissue, and a culture of a cell or a microorganism.

5. A kit for detecting acharan sulfate present in a sample, comprising at least one antibody according to claim 1.

6. The detection kit according to claim 5, wherein the sample is selected from the group consisting of a body fluid, a cell, a tissue and a culture of a cell or a microorganism.

* * * * *

UNITED STATES PATENT AND TRADEMARK OFFICE
CERTIFICATE OF CORRECTION

PATENT NO. : 7,915,389 B2
APPLICATION NO. : 12/297048
DATED : March 29, 2011
INVENTOR(S) : Suzuki et al.

It is certified that error appears in the above-identified patent and that said Letters Patent is hereby corrected as shown below:

Title Page, item (56), Other Publications
Page 1, Column 2, Line 12 "*Achatina fluica*,"" should be changed to --*Achatina fulica*,"--
Sheet 1 of 4, Fig. 1, Line 8, "Carbohyddr. Lett." should be changed to --Carbohyrdr. Lett--
Sheet 1 of 4, Fig. 1, Line 11, "Methods Carbohyrdr." should be changed to --Methods Carbohydr.--
Column 1, Line 45, "NAC-NSH;" should be changed to --NAc-NSH;--
Column 1, Line 45, "1996" should be changed to --1996.--
Column 2, Line 2, "pp. 38346-38352, 2004" should be changed to --pp. 38346-38352, 2004.--
Column 3, Line 1, "to the above (15)" should be changed to --to the above (15),--
Column 3, Line 43, "WHITE MATTER" should be changed to --WHITE MATTER.--
Column 9, Line 55, "NAC-HEP," should be changed to --NAc-HEP,--
Column 9, Line 57, "NAC-NSH," should be changed to --NAc-NSH,--
Column 10, Line 17, "0.1 MMES buffer" should be changed to --0.1 M MES buffer--
Column 12, Line 56, "BlockAce" should be changed to --Block Ace--
Column 15, Line 60, "µg/well)" should be changed to --µg/well).--
Column 16, Line 42, "with NAC-HEP" should be changed to --with NAc-HEP--
Column 18, Line 27, "detecting the present" should be changed to --detecting the presence--

Signed and Sealed this
Third Day of April, 2012

David J. Kappos
*Director of the United States Patent and Trademark Office*